United States Patent [19]
Fillaud

[11] Patent Number: 5,371,329
[45] Date of Patent: Dec. 6, 1994

[54] DEVICE FOR SIMULTANEOUS WEIGHING AND AGITATION

[75] Inventor: G. Alain Fillaud, Aix en Provence, France

[73] Assignee: Hemopharm Service, Gardan, France

[21] Appl. No.: 30,456
[22] PCT Filed: Sep. 30, 1991
[86] PCT No.: PCT/FR91/00763
§ 371 Date: Apr. 1, 1993
§ 102(e) Date: Apr. 1, 1993
[87] PCT Pub. No.: WO92/05812
PCT Pub. Date: Apr. 16, 1992

[30] Foreign Application Priority Data
Oct. 1, 1990 [FR] France ............... 90 12269

[51] Int. Cl.$^5$ ............... G01G 19/52; G01G 13/02
[52] U.S. Cl. ..................... 177/245; 177/118; 128/DIG. 13
[58] Field of Search ............... 177/118, 245; 128/33, 128/36

[56] References Cited
U.S. PATENT DOCUMENTS

| 3,557,789 | 1/1971 | Poitras | 177/118 X |
| 3,698,494 | 10/1972 | Gaudin | 177/118 |
| 3,924,700 | 12/1975 | Lindsey et al. | 177/118 |
| 4,027,735 | 6/1977 | Floyd | 177/118 |

FOREIGN PATENT DOCUMENTS
2088635 12/1971 France .

Primary Examiner—George H. Miller, Jr.
Attorney, Agent, or Firm—Dvorak and Traub

[57] ABSTRACT

The device for simultaneous weighing and agitation comprises a tray (14) for receiving an object (15) to be weighed, which object is a receptacle (15) for progressively receiving a substance (18), and the tray (14) is associated both with means (16) enabling the weight of said object to be measured, and with means (1) enabling agitation motion to be imparted thereto. The tray (14) and the agitation means (1) are mounted on a common support (17) on which exact measurement is then performed with an error of not more than 5% of the weight of the combined device and object (15) to be weighed during agitation.

10 Claims, 3 Drawing Sheets

DEVICE FOR SIMULTANEOUS WEIGHING AND AGITATION

DESCRIPTION

The present invention relates to a device for simultaneous weighing and agitation.

The technical sector of the invention is the field of constructing an electronic precision balance.

One of the main applications of the invention is making weighing or balancing devices that simultaneously agitate the balance tray that receives the element to be weighed, which element may be a bag for collecting blood. Other applications can also be envisaged in industrial fields that also require a substance to be weighed with fairly high accuracy while maintaining a degree of agitation so as to mix the substance with another during weighing, as may occur in the manufacture of perfumes, of medicines, of paints, . . .

In the field of withdrawing blood, equipment already exists enabling blood to be withdrawn while satisfying standards laid down by the authorities, which in France means a maximum of 7 ml/kg of donor weight and a maximum take of 450 ml. In addition, the blood withdrawn must be mixed with an anticoagulant which is already contained in the collection bag.

For the purpose of assisting operators in collecting blood in compliance with these standards, and thus while monitoring as accurately as possible the quantity taken from a donor, patent applications have been made for various devices, for example:

Patent application No. 2 514 893 filed Oct. 19, 1981 by MCB: that application describes a method and a device for programmable weighing of a mixture in suspension having one of its constituents being added progressively thereto, with the constituents being agitated periodically; it is used in particular for mixing blood that is withdrawn progressively from a donor with an anticoagulant. The characteristic of that apparatus is that after each period of agitation, inflow of the external constituent is interrupted during each weighing operation and the apparatus includes means for stopping the alternating operations of inflow agitation and of weighing once a weighing operation indicates that a certain predetermined weight has been reached.

French patent application 2 548 135 filed May 19, 1983 by Vibration Internationale SARL describes an installation for filling flexible containers on balance pans with accompanying vibration. Those installations do not relate to the field of withdrawing blood and they are applicable to containers in the form of cylindrical bags having respective filling valves. The system described includes a frame that vibrates during said filling, and between two filling sequences, the frame is placed on a weighing platform situated therebeneath by vertical displacement of the container on said weighing tray.

The drawbacks of the two above systems are essentially that the weight of the liquid inserted into the bag or the container is not measured continuously, so good measurement accuracy is not possible since accuracy may drift between two readings, and secondly since agitation is also interrupted while the measurement is being performed, it is not possible to guarantee that the substance is homogeneous, and when the substance is blood that can be a major therapeutic drawback. This latter criterion also applies to patent application No. 2 603 190 to Centre Régional de Transfusion Sanguine, filed by Mr. MASSE et al., on Aug. 29, 1986 and relating to a method and apparatus for quantitative monitoring of withdrawal and also to a method and an installation for withdrawing blood from a donor for treatment purposes: the apparatus comprises a stand, a container support, and means for measuring a parameter related to the quantity withdrawn, and various other additional means. The applicant specifically claims the fact that the support is stationary and that there is no substantial agitation of the blood in the container: in the present invention that is considered as being a major drawback, as mentioned above.

To satisfy this object of simultaneous weighing and agitation, various other patent applications are also known:

Patent application No. 2 574 540 filed on Dec. 10, 1984 by Mr. BRUNET, and certificate of addition applications Nos. 2 544 220 and 2 567 416 filed on Apr. 14, 1983 and Jul. 12, 1984 by Mr. BAUDRY: those various applications concern a balance system associated with an agitator for use in withdrawing blood. Those three systems are not in fact genuine balances since they essentially comprise a spring compensation system that can be set to a determined value; when the balance tray receiving the inflow under consideration reaches a previously set reference level, a lever mechanism stops the agitation and stops said inflow. In addition, in all three cases under consideration, it is misleading to use the term "balance" for the system since no measurement is taken, the system being based on spring means that the inventors themselves mention provides accuracy only to about 50 grams (g) for weights in the range 450 g to 600 g. This constitutes a very wide margin of error that is difficult to make compatible with the characteristics of the centrifuges in which the blood is subsequently treated to prepare it for medical use.

Finally, Japanese applications JP No. 176584 of Nov. 19, 1986 and No. 74240 of Mar. 30, 1987 in the name of Kabushiki Kaisha relate to apparatus and a method for collecting constant quantities of blood from individual donors. The various devices described are amongst the most elaborate yet known since they do indeed allow the bag of blood placed on the device concerned to be simultaneously weighed and agitated by piezoelectric measurement means coupled to the weighing tray; the tray and cell assembly is mounted as a unit on a fixed horizontal shaft enabling the entire system to be tilted by rocking means. This has the drawback that accurate weighing measurements can be taken during each oscillation only when the system returns to the same initial point, i.e. only once every 2 or 3 seconds. If measurement is performed continuously, that gives rise to measurement errors of about 3% by weight even if correction is performed, because of the angular deviation of the cradle.

All of those weighing systems with or without simultaneous agitation are thus very crude and do not enable high measurement accuracy to be achieved, given the crude choice of technical means which either do not enable simultaneous agitation, or do not enable any agitation at all, or else are not very accurate even when using sophisticated technical means. This is most disadvantageous since if the standards are exceeded, then the legal or medical consequences applicable to withdrawing blood, for example, may be severe, while if operators stay well below the standards as a precaution, then that costs them very dear given the very high unit cost of a bag of blood; in addition, blood must then be treated by centrifuging, and centrifuging requires accuracy to better than the 10% provided by most present apparatuses. Furthermore, some of those apparatuses do not provide the operator with all of the functions (other than simultaneous weighing and agitationá that are specific to withdrawing blood, e.g. clamping the tube at the end of withdrawal with automatic monitoring, and programming on demand.

The problem posed is to implement weighing of an object with simultaneous agitation thereof, which object may be a bag containing liquids, one of which is flowing in continuously, e.g. blood from a donor; the weighing must be performed with accuracy that is compatible with predetermined weight conditions and tolerance constraints as a function of the desired use.

Another object is to be able to monitor the quantity of liquid transferred into the bag during weighing so as to stop the transfer at a predetermined value which is a function firstly of pre-established conditions and secondly of conditions that are verified and measured in situ, and to inform the operators of all of the data specific to the operation performed.

Finally, another object is to stop said weighing-agitating-transfer operation automatically and reliably when the desired conditions are achieved.

One solution to the problem posed is a device for simultaneous weighing and agitation comprising a tray for receiving an object to be weighed, which object is a receptacle progressively receiving a substance, and the tray is associated firstly with means enabling the weight of said object to be weighed, and secondly with means imparting agitation motion thereto; according to the invention, the tray and the agitation means are mounted on a single support on which exact measurement is then performed with an error equal to not more than 5% of the combined weight of the apparatus and the object to be weighed during agitation; said error being preferably equal to not more than 1%.

Another object of the invention is achieved by a device for simultaneous weighing and agitation as described above used for weighing a collecting bag being filled progressively with blood via a tube, which apparatus includes a clamping system for said tube to compress it and close it at the end of the operation.

Another object of the present invention is provided by a method for simultaneous weighing and agitation for use in withdrawing blood by means of a device including a tray for receiving a bag in which said blood can be received, means for measuring the weight of said bag, and means transmitting agitation motion thereto, such that:

said bag is placed on said tray and the blood feed tube is placed in the clamping device which is placed in a locking situation by means of a detector for detecting the presence of said tube;

a keypad connected to a controlling microprocessor for the apparatus is used for programming the volume of blood to be withdrawn as a function of various parameters, e.g. such as: the volume of said bag; the weight of the donor in compliance with standards laid down; direct programming of the volume to be withdrawn, regardless of the weight and the number of bags, or two or more of these conditions;

the assembly comprising the agitation means, the tray, the bag and the blood is weighed continuously, said assembly being supported on a common support bearing on said measuring system;

said tray is simultaneously and continuously agitated throughout the entire duration of the blood-withdrawal operation;

withdrawal is stopped by closing the clamping device when the volume of blood contained in the bag has reached the volume which corresponds to the initially programmed volume; and the end of the operation and termination of any information relating to said operation is displayed or conveyed to the operator by any means.

The result is novel devices for simultaneous weighing and agitation and a novel method using said devices specially adapted to withdrawing blood. They make it possible to satisfy the requirements of operators essentially because of the possibility provided by the system of obtaining great measurement accuracy, which may achieve one part per thousand of the weight of the object to be weighed even while it is being agitated, whereas accuracy of 1% is sufficient for the application under consideration.

The design of previously-available equipment as described above does not enable such accuracy to be obtained, and it can be obtained by the present invention essentially because measurement and weighing relate to the entire device including the agitation system: by subsequently filtering the measurement reading, the agitation does not give rise to measurement errors as in other systems that are related to the rotary and vibration displacement of the masses and of the sensors which are themselves put into motion by the agitation system. In addition, the techniques and the ways of assembling the agitation system and the measurement system as described below ensure and add to the above characteristic for the desired result. For reasons relating to the homogeneous quality of the mixture, which reasons are particularly necessary when withdrawing blood, the idea is to agitate the object to be weighed while simultaneously weighing it, and without interrupting the agitation, even for a few fractions of a second.

Another advantage of the present invention is to be able to provide equipment essentially for withdrawing blood that integrates all of the functions required therefor, which has not been done by any equipment available in the past, which functions, then taken together, allow the apparatus to operate on its own, thereby reassuring the operator and relieving the operator of monitoring constraints, thereby enabling the operator to concentrate on more complex tasks and thus avoiding errors. It should not be forgotten that exceeding the standards may be harmful for the donor and, in contrast, taking blood donations that are too small can be expensive for a blood-collection center which subsequently treats the blood, since the cost of treatment is the same regardless of the weight of a bag, without mentioning problems of adjusting the centrifuges as a function of the known weight of each bag.

The further possibility of making the device waterproof provides greater comfort to the operator who can inadvertently spill any liquid without fear of damaging the apparatus.

Other advantages of the present invention could be mentioned, but those given above suffice to demonstrate the novelty and the advantages thereof. The following description, drawings, and figures show an embodiment of the invention, but they are not limiting in any way: other embodiments are possible on the basis of the claims which specify the scope and the extent of the invention, and in particular the apparatus for simultaneous weighing and agitation may be used in applications other than withdrawing blood, and it may be used with objects whose weights go up to several hundreds of kilograms.

Figure 1:
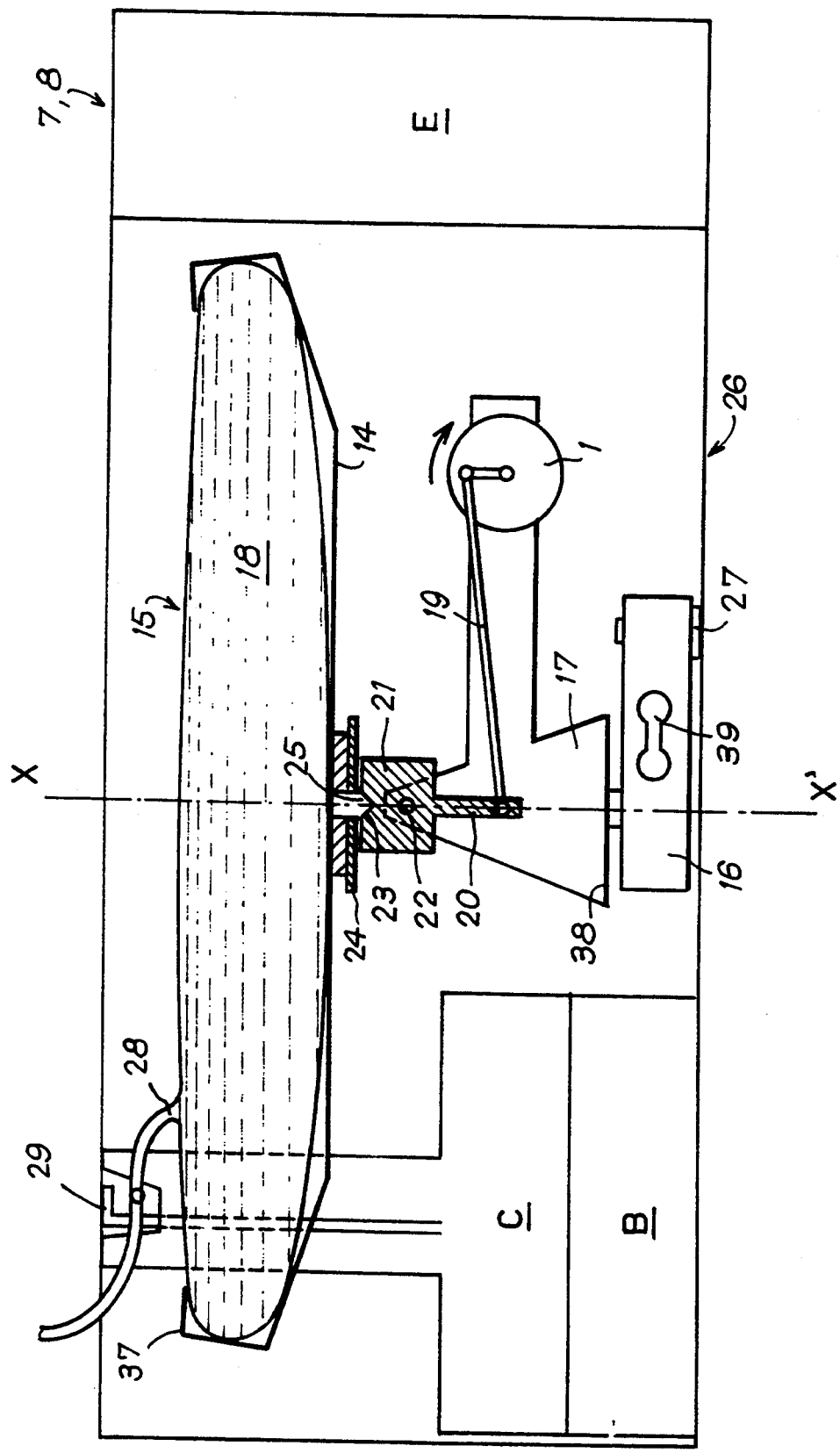
FIG. 1 is a view in section and in profile of a system of the invention for simultaneous agitation and weighing.
Figure 4:
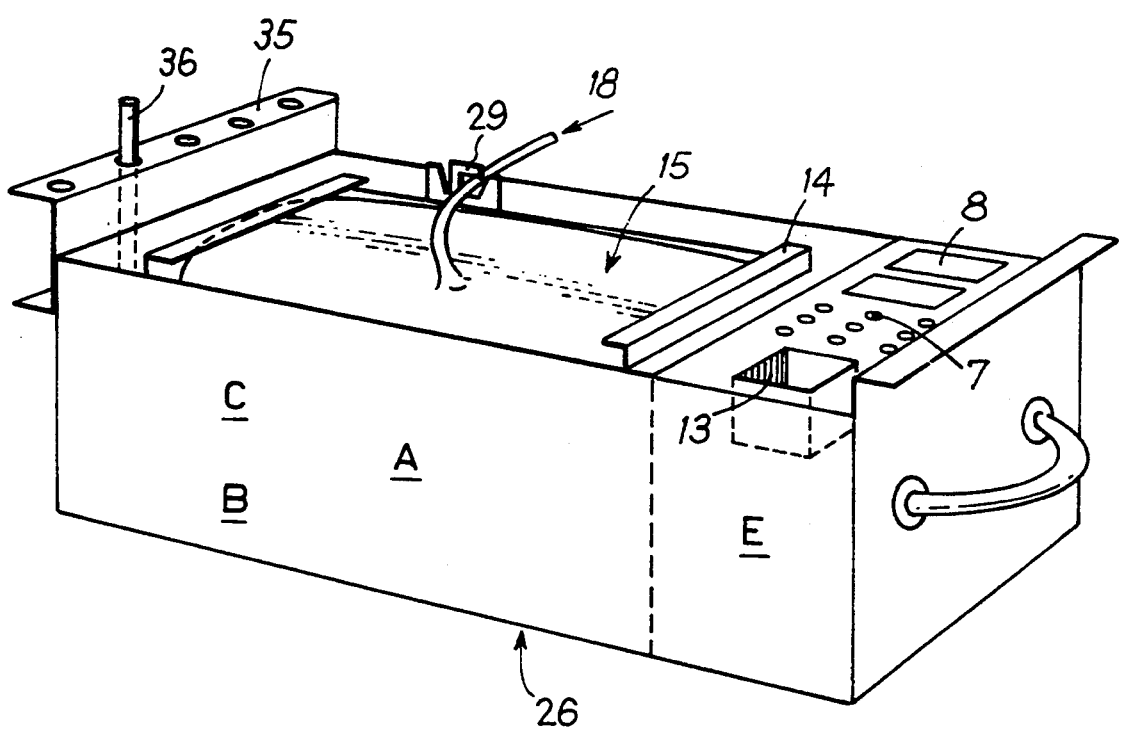
FIG. 4 is a perspective view of a stand in which the entire apparatus of the invention is integrated.

FIG. 1 is a simplified longitudinal section view of the stand 26 shown in perspective in FIG. 4 and in which the following are presented diagrammatically only: the electrical and electronic portion E including its keypad 7 and screen 8 on top; the battery block B; and the clamping system C, 29. This figure is thus for use essentially in describing the system A for weighing and for agitation.

This system comprises a tray 14 receiving the object 15 to be weighed: in the non-limiting present example, said object is a blood-collecting bag 18 including a tube 28 passing beneath the bracket 29 of the clamping device described with reference to FIG. 2. In this example, the tray 14 is raised at both ends so as to match the natural shape of the bag 15 and limit the amplitude of motion of the liquid 18 during agitation: the tray may be made of metal such as aluminum, but it could also be replaced by any receptacle such as a jar. The tray may also include rims 37 extending inwardly from each end over a bag 15 for the purpose of holding it. The tray is placed directly on the agitation and weighing apparatus which includes a top thrust bar 21, also referred to an agitation bar. The bar may be made of steel and include a centering hole 23 on the weighing axis XX', and said tray may include a magnetic plate 24 and a centering stud 25, the plate and the stud co-operating with the bar 21 and the hole 23 to hold the tray on said bar 21 and to enable the tray and the object to be withdrawn easily.

The agitation means is essentially constituted by an electric motor mounted on the support 17 that receives the assembly of devices for agitation of the tray and of the object to be weighed, the motor being cantilevered out from the vertical weighing axis XX' of the assembly. The motor 1 rotates one end of a connecting rod 19 whose other end is connected to a lever 20 secured to the agitation bar 21 which is itself mounted on a horizontal axis 22, free to rotate relative to the support 17 supporting said tray 14 and situated in a plane that contains the measurement axis XX'.

In a preferred embodiment, this disposition makes it possible to place the axis of the motor 1 in the same horizontal plane as the connection between the connecting rod 19 and the lever 20, thereby making it easier by measurement integration and filtering to eliminate parasitic force components that could be produced by the rotary and translation motion. In order to obtain the gentle and continuous agitation that is required for ensuring that the substance to be conserved in the bag 15 is homogeneous, the motor 1 preferably rotates at a speed of about 10 revolutions per minute. The motor is designed to deliver sufficient torque to displace the lever 20 given the weight of the objects to be supported by the tray 14. In addition, in order to avoid any deformation and/or vibration of the support 17 which is required to provide rigid fixing for the motor 1, for the bar 21 receiving the tray and its load, and for itself on the weighing measurement system 16 on the axis XX' along which it transmits the entire weight of the assembly, it is necessary to balance the distribution in a vertical plane of the centers of gravity of the motor 1, of the tray, and of its load. Likewise, it is necessary to balance the motor 1 relative to the drive system for the lever 20 and to provide stiffeners on the support 17. The support is preferably a stirrup-shaped member whose base 38 bears against the measurement system 16 and whose two side portions receive firstly the axis 22 of the agitation bar 21 which is situated between them at their top ends, and secondly said motor 1 in a cantilevered out position.

In a preferred embodiment, the weighing means 16 is a bar that deforms and that includes a strain gauge, with the free end of the bar receiving the support 17 supporting the tray assembly 14, the object to be weighed 15, and the stirring means 1 on the weighing axis XX', and having a fixed end 27 secured to the stand 26 of the apparatus. The deformation bar 16 preferably has a through hole at its center 39 and preferably includes a known "binocular" type strain gauge that is temperature compensated and calibrated to enable weighing to be performed to within one gram up to a total weight of 3,000 grams. A weighing measurement is preferably taken 250 times per millisecond, which can be considered as constituting continuous measurement, thereby making it subsequently possible to perform filtering that eliminates all cyclic variations that may exist such as those due to motion of the liquid or to a shock. This very high rate of sampling, and the way in which the linking parts are selected and assembled thus makes it possible to obtain a volume measurement to within one ml, for a total volume of 1,000 ml, i.e. to within one part in 1,000.

Figure 2:
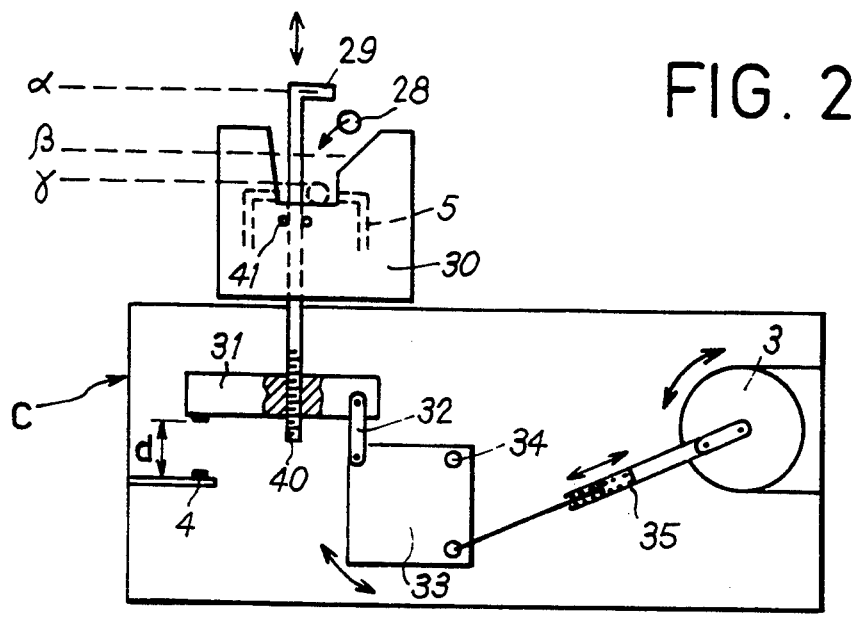
FIG. 2 is a profile view of the clamping system.

FIG. 2 is a longitudinal profile view of the clamping system C shown diagrammatically in FIG. 1. This system comprises a vertical bracket 29 that is curved over at its top end and that slides in a notched guide part 30 having an outwardly directed V-shaped opening for receiving the tube 28. The bracket 29 has its bottom end fixed to a drive part 31 which is in turn fixed to a crank 33 hinged about a fixed axis 34 and driven on its side opposite from said drive part 31 by a connecting rod 43 controlled by an electric motor 3.

The electric motor 3 may be the same as the agitation motor 1. It is reversible and is capable of performing a complete revolution under stepper control to be able to stop in any position. The bracket 29 can take up three positions $\alpha$, $\beta$, and $\gamma$ along its vertical axis, and it is monitored by a height-measuring sensor 4 which controls the rotation of said motor 3.

The high position $\alpha$ corresponds to a wide open position for engaging or disengaging the tube 28; intermediate position $\beta$ serves to hold the tube in position without crushing or deforming it; and the low position $\gamma$ squeezes the tube completely so as to prevent any fluid such as blood flowing therealong. These three positions are detected and monitored by a distance sensor 4, which may be an optical diode and whose accuracy is of the order of 0.5 mm in measuring the distance between a stationary portion secured to the stand and the drive part 31 which is itself set at an appropriate height relative to the bracket 29 by means of a thread 40. To ensure that the bracket moves vertically without deformation since that would spoil the measurement, a link 32 connects the drive part 31 to the crank 34. To avoid damaging the tube 28 or the drive system, the connecting rod 43 is a spring rod capable of absorbing the differences of diameter presented by said tube 28 and thereby avoiding any risk of damage in the event of a rigid part becoming jammed beneath the bracket 29.

Figure 3:
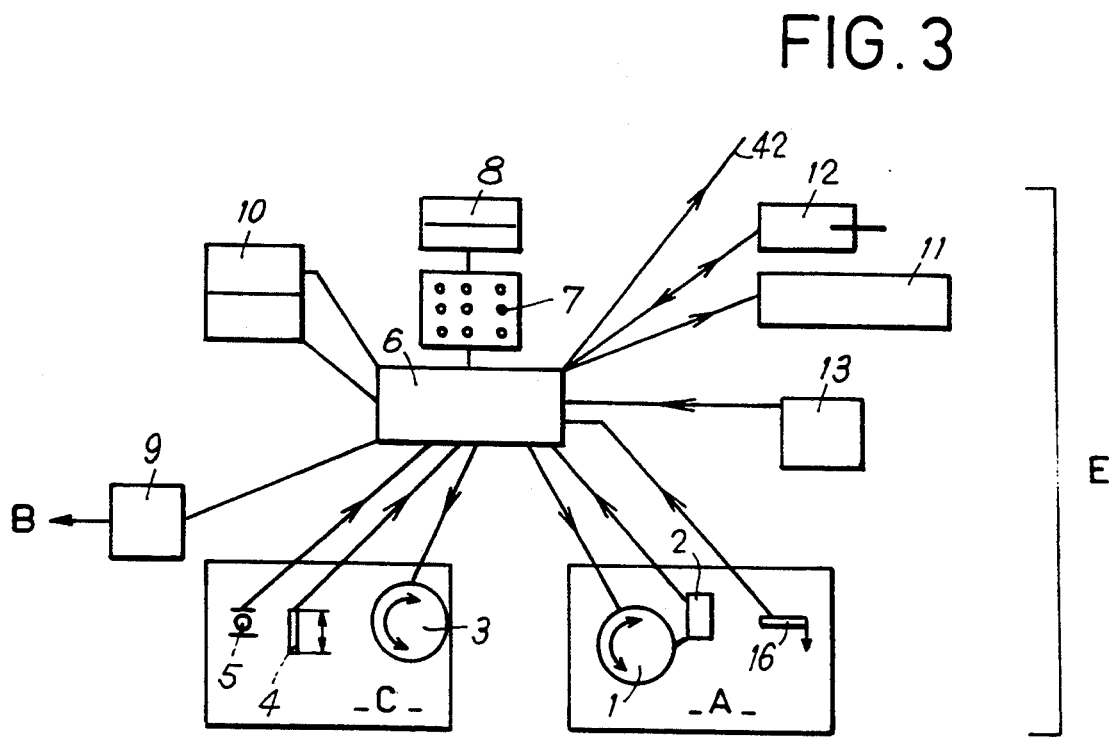
FIG. 3 is a diagram showing the operation of the electronic system for agitation and for weighing.

In order to enable the apparatus as shown in FIG. 4 and as shown diagrammatically in FIG. 3 to be self-contained and reliable, the stationary block or guidance part 30 includes diode type sensors 5 at the bottom of its V-shaped opening serving to detect the presence or the absence of the tube 28 so as to prevent operation so long as a tube is not installed and so as to ensure that it is held by the bracket 29 once it has been installed. This presence detector may also measure the optical density of the tube and thus deduce the corresponding diameter thereof, e.g. to within one millimeter, and this can subsequently be integrated in the control applied to the motor 3 and in the vertical position measurement provided by the sensor 4 to take account specifically of possible changes in diameter and to avoid crushing while holding the tube, in addition to the safety provided by the spring connecting rod 43.

Finally, a sealing ring 41 secured in the block 30 around the bracket 29 provides sealing for the system against any possible liquid spill.

FIG. 3 is a diagram showing the operation of apparatus integrating all of the above-described functions, and possibly other functions too, in an application to withdrawing blood, and comprising, in particular a monitoring and controlling microprocessor 6. This integrated apparatus makes it possible, in particular, to monitor and perform the method as described with reference to the preceding figures. Thus, the microprocessor 6 is associated with EPROM type memories 10 having a capacity of at least 8 kilobytes for storing its controlling program and system program, and a RAM type memory of 256 kilobytes, for example, for operating purposes. A keypad 7 makes it possible to key in data manually relating to the method and to other functions. A display 8 of any known type provides the information required by an operator to enable data to be confirmed, to monitor how the operation is progressing, and to obtain a display of results. The data may also be output on a printer 11 connected to the microprocessor 6. It may optionally be integrated in the apparatus, e.g. enabling stick-on labels to be printed for application to the collection bag 4 so as to identify its characteristics and the characteristics of the donor.

A personalized card reader 12 and/or a link to any other external microcomputer 42 may also be connected and added to the system.

The microprocessor charges and monitors charge in rechargeable batteries 9 (preferably 12 V batteries) required to enable the assembly to operate, and thus, either from its internal program or under control from the keypad 7, it runs various functions such as:

the agitation and weighing system A using the motor 1 and the measurement sensor 16 as described above, together with a position sensor 2 for the motor to ensure that the tray 14 is always stopped in the same position after blood has been withdrawn, e.g. horizontal;

the clamping system C with its motor 3, position sensor 4 and tube presence detector 5 as described above; and one or more analysis tests on the blood to be withdrawn, prior to starting withdrawal proper and using any known system 13 integrated in the apparatus, which system serves to determine blood withdrawal options as a function of the results of biological tests; the system thus makes it possible by calculation means internal to the program and as a function of the various parameters taken into account, to determine the net volume that may be withdrawn, and thus the maximum limit on the total volume that can be withdrawn as a function of the blood of the donor, which limit can then be used for programming said apparatus.

This option is of particular interest in an operating theater for indicating intentional normal hemodilution and also in transfusion predosing.

These tests may essentially be hemoglobin and/or hematocrit tests in which the blood is caused to react with consumable reagents that serve, in some cases depending on the results obtained, to limit the volume withdrawn to less than the standard limit or, on the contrary, to enable more blood to be withdrawn, if necessary, as when preparing for an operation. Operators can then decide themselves on the final volume to be withdrawn, or on the contrary, they may rely on the apparatus if the microprocessor has an appropriate program associated therewith.

FIG. 4 is an overall perspective view of apparatus comprising a stand 26 in the form of a moistureproof box in which the weighing and agitation system A and the clamping system C are disposed together, and which also includes an electronics portion E containing at least one microprocessor 6 controlling the various weighing, agitation, and clamping functions as described above, a keypad 7 for keying in the information required for operation of said microprocessor, a display 8, and a set of batteries B, 9 to make the apparatus self-contained.

On at least one of its sides, the stand 26 may include a rack 35 capable of receiving a plurality of test tubes 36 for storing samples of the blood being withdrawn.

This figure also shows the blood-collecting bag 15 and its tube 18 placed on the tray 14, together with the integrated biological analysis test system 13 represented in this case by an opening suitable for receiving a test tube and having sensors enabling said test to be performed disposed around the opening and beneath it. The stand 26 may be closed by a cover and may be transportable by means of handles. The bottom portion of the stand may receive an ink jet type printer in the form of a removable lateral drawer, for the purpose of printing labels that are subsequently stuck on said bags, and also a personal card reader, and any other additional functions.

I claim:

1. A device for simultaneous weighing and agitation, said device comprising a tray for receiving an object to be weighed, said object being a receptacle that progressively receives a substance, said tray being associated firstly with weight measurement means enabling the weight of said object to be measured and secondly with agitation means enabling agitation motion to be imparted thereto, said agitation means comprising an electric motor off-set from a vertical weighing axis of said tray and rotating one end of a lever arm for rocking an agitation bar mounted on a horizontal axis and being free to rotate said bar supporting said tray, wherein said tray and said agitation means are mounted on a single support on which weight measurement is then performed by weight measurement means, which measures the weight of the assembly along said vertical weighing axis, said weight measurement means having a weight measurement error equal to not more than 5% of the combined weight of the device and the object to be weighed during agitation.

2. A device for simultaneous weighing and agitation according to claim 1, wherein said weight measurement means include a bar having a top steel thrust member and a centering hole on said weighing axis, said tray including a magnetized plate and a centering stud, which plate and which stud cooperate with said bar and said hole to hold said plate on said bar and to enable said tray and said object to be withdrawn easily.

3. A device for simultaneous weighing and agitation according to claim 1, wherein said weight measurement means comprises a deformable bar including a strain gauge, a free end of said bar receiving said support on said weighing axis at a location where it supports an assembly comprising said tray, said object thereon to be weighed, and said agitation means, wherein a stationary end of said deformable bar is secured to a stand of said device.

4. A device for simultaneous weighing and agitation according to claim 1, said device being used for weighing a bag for collecting blood, said bag being filled progressively via a tube, said device including a clamping system for clamping said tube to compress it and close it on completion of withdrawing blood, wherein said clamping system comprises a vertical bracket curved over at its top end and sliding in a notched guide part having an upwardly directed V-shaped opening for receiving said tube, said bracket having its bottom portion fixed to a drive part, said drive part being connected to a crank hinged about a stationary axis and driven on a distal side opposite to a proximate side connected to said part by a connecting rod controlled by an electric motor.

5. A device for simultaneous weighing and agitation according to claim 1, wherein said bracket has up to three bracket positions monitored by a height measurement sensor that controls rotation of said motor.

6. A device for simultaneous weighing and agitation according to claim 4, wherein said connecting rod is a spring rod capable of compensating differences in diameter of said tube.

7. A device for simultaneous weighing and agitation according to claim 4, further comprising a stand in the form of a moistureproof box in which said weight measurement means, said agitation means, and said clamping systems are disposed together, said moistureproof box also having an electronic element comprising at least a microprocessor that controls weighing, agitation, and clamping functions, a keypad to receive information required for the operation of said microprocessor, a display, and a set of self-contained batteries.

8. A device according to claim 7, wherein said stand has a rack on at least one of its sides suitable for receiving a plurality of test tubes for storing samples of blood being withdrawn.

9. A method for simultaneous weighing and agitation of withdrawn blood by means of a device including a tray for receiving a bag in which said blood can be received, means for measuring the weight of said bag, and means for transmitting agitation motion thereto, comprising the steps of:

placing said bag on said tray, placing a blood feed tube in the clamping device, and locking said tube in said clamping device by means of a detector for detecting the presence of said tube;

programming via a keypad connected to a controlling microprocessor the volume of blood to be withdrawn as a function of various parameters, e.g. such as: the volume of said bag; the weight of the donor in compliance with specified standards; or direct programming of the volume to be withdrawn;

supporting an assembly comprising said agitation means, said tray, and said bag on a common support bearing of said measuring means;

withdrawing blood into said bag;

simultaneously and continuously agitating said bag throughout the entire duration of the blood-withdrawal operation;

stopping withdrawal by closing the clamping device when the volume of blood contained in the bag has reached the volume which corresponds with an initially programmed volume; and displaying or conveying information relating to said blood withdrawal operation to device operating personnel.

10. A method for simultaneous weighing and agitation according to claim 9, further comprising the step of performing a biological analysis test on the blood to be withdrawn using an analysis system integrated in the device, indicating through the system the maximum limit on the total volume that may be withdrawn as a function of the donor's blood, and programming said device based on the system indication.

* * * * *